United States Patent [19]

Weber et al.

[11] 4,180,573
[45] Dec. 25, 1979

[54] 1-PIPERAZINO-6-PHENYL-4H-S-TRIAZOLO[3,4-c]THIENO[2,3-e]1,4-DIAZEPINES

[75] Inventors: Karl-Heinz Weber; Adolf Langbein, both of Gau-Algesheim; Claus Schneider, Ingelheim am Rhein; Erich Lehr, Waldalgesheim; Karin Böke, Ingelheim am Rhein; Franz J. Kuhn, Bingen, all of Fed. Rep. of Germany

[73] Assignee: Boehringer Ingelheim GmbH, Ingelheim am Rhein, Fed. Rep. of Germany

[21] Appl. No.: 924,149

[22] Filed: Jul. 13, 1978

[30] Foreign Application Priority Data

Jul. 21, 1977 [DE] Fed. Rep. of Germany ....... 2732921
Jul. 21, 1977 [DE] Fed. Rep. of Germany ....... 2732943

[51] Int. Cl.² .............. A61K 31/495; C07D 295/16; C07D 295/08
[52] U.S. Cl. .................................... 424/250; 424/251; 260/243.3
[58] Field of Search ..................... 260/243.3; 424/250, 424/251

[56] References Cited

U.S. PATENT DOCUMENTS 4,017,620  4/1977  Kuwada et al. .................. 260/243.3

Primary Examiner—Jose Tovar
Attorney, Agent, or Firm—Hammond & Littell

[57] ABSTRACT

Compounds of the formula wherein
$R_1$ is hydrogen, lower alkyl, halo-lower alkyl, hydroxy-lower alkyl, di(lower alkyl)amino-lower alkyl, phenyl, tolyl, methoxy-phenyl, nitro-phenyl, halo-phenyl, pyridyl, pyrimidinyl or —CO—$R_4$, where $R_4$ is hydrogen, alkyl or 1 to 17 carbon atoms, alkoxy of 1 to 2 carbon atoms, phenyl, tolyl, methoxy-phenyl, halo-phenyl, nitro-phenyl or pyridyl;
$R_2$ is hydrogen, fluorine, chlorine, or bromine; and
$R_3$ is chlorine, bromine or lower alkyl, and non-toxic, pharmacologically acceptable acid addition salts of certain of these compounds. The compounds as well as the salts are useful as anxiolytics, tranquilizers, sedatives or neuroleptics.

10 Claims, No Drawings

1-PIPERAZINO-6-PHENYL-4H-S-TRIAZOLO[3,4-c]THIENO[2,3-e]1,4-DIAZEPINES

This invention relates to novel 1-piperazino-6-phenyl-4H-s-triazolo[3,4-c]thieno[2,3-e]1,4-diazepines and acid addition salts of certain of these compounds, various methods of preparing them, pharmaceutical compositions containing them as active ingredients, and methods of using them as anxiolytics, tranquilizers, sedatives or neuroleptics.

More particularly, the present invention relates to a novel class of compounds represented by the formula

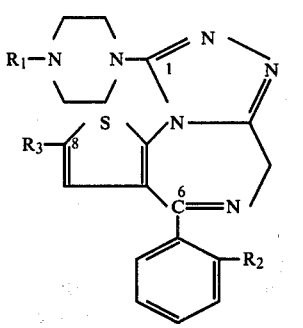

(I)

wherein
$R_1$ is hydrogen, lower alkyl, halo-lower alkyl, hydroxy-lower alkyl, di(lower alkyl) amino-lower alkyl, phenyl, tolyl, methoxy-phenyl, nitro-phenyl, halo-phenyl, pyridyl, pyrimidinyl or —CO—$R_4$, where $R_4$ is hydrogen, alkyl of 1 to 17 carbon atoms, alkoxy of 1 to 2 carbon atoms, phenyl, tolyl, methoxy-phenyl, halo-phenyl, nitro-phenyl or pyridyl;
$R_2$ is hydrogen, fluorine, chlorine or bromine; and
$R_3$ is chlorine, bromine or lower alkyl;
and non-toxic, pharmacologically acceptable acid addition salts of certain of these compounds.

The term "lower alkyl" as used herein is intended to designate alkyl of 1 to 6 carbon atoms; the preferred embodiment is straight or branched alkyl of 1 to 3 carbon atoms.

Preferred embodiments of the terms "halo" or "halogen" are fluorine, chlorine, bromine or iodine.

Preferred embodiments of di(lower alkyl)amino-lower alkyl are dimethylamino-methyl, dimethylamino-ethyl, diethylamino-methyl and diethylamino-ethyl.

In those instances where $R_1$ and/or $R_4$ represent substituted phenyl, the substituent may be in the o-, m- or p-position. Likewise, pyridyl may be 2-,3- or 4-pyridyl.

When $R_4$ is alkyl, the preferred embodiment is straight or branched alkyl of 1 to 6 carbon atoms.

Thus, a sub-genus under the genus defined by formula I is constituted by those compounds where $R_1$ is hydrogen, alkyl of 1 to 3 carbon atoms or hydroxy-(alkyl of 1 to 3 carbon atoms); $R_2$ is chlorine; and $R_3$ is bromine, and non-toxic, pharmacologically acceptable acid addition salts thereof.

Another sub-genus is constituted by those compounds of the formula I where $R_1$ is phenyl or pyridyl, $R_2$ is chlorine, and $R_3$ is bromine.

Finally, still another sub-genus is constituted by those compounds of the formula I where $R_1$ is —CO—$R_4$, where $R_4$ is hydrogen or methyl, $R_2$ is chlorine, and $R_3$ is bromine.

The compounds embraced by formula I may be prepared by the following methods:

Method A

By reacting a triazolo-thieno-diazepine of the formula

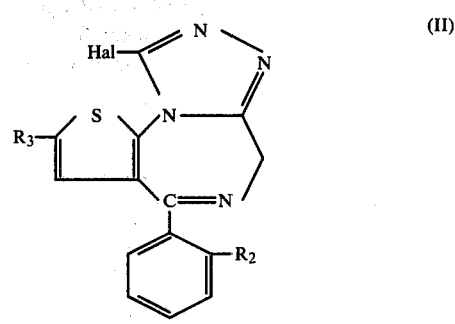

(II)

wherein
$R_2$ and $R_3$ have the same meanings as in formula I, and
Hal is halogen,
with a piperazine of the formula

(III)

wherein $R_1$ has the same meanings as in formula I.

The reaction may be performed without a solvent or in a high-boiling-point solvent such as benzene, toluene, dioxane, tetrahydrofuran or a chlorinated hydrocarbon such as carbon tetrachloride or methylene chloride, preferably at the boiling point of the particular solvent which is used. The reaction time depends upon the particular starting compound which is used and may range from a few minutes to several hours.

Method B

By de-hydrogenating a 1-piperazino-6-phenyl-5,6-dihydro-4H-s-triazolo[3,4-c]thieno[2,3-e]1,4-diazepine of the formula

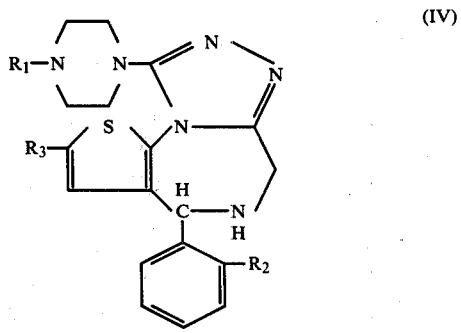

(IV)

wherein $R_1$, $R_2$ and $R_3$ have the same meanings as in formula I.

The de-hydrogenation is effected with, for example, a halogen or a compound of the higher oxidation stages of chromium or manganese, such as a chromate, a bichromate or a permanganate, in the presence of a solvent.

Suitable solvents for the de-hydrogenation with a halogen are, for example, chlorinated hydrocarbons such as chloroform or methylene chloride. Examples of solvents suitable for the de-hydrogenation with the compounds of chromium or manganese are acetone, tetrahydrofuran or dioxane.

Depending upon the type of de-hydrogenating agent, the reaction temperature is between 0° C. and the boiling point of the particular solvent which is used.

Method C

For the preparation of a compound of the formula I wherein $R_1$ is —CO—$R_4$, by acylating a 1-piperazino-6-phenyl-4H-s-triazolo[3,4-c]thieno-[2,3-3]1,4-diazepine of the formula

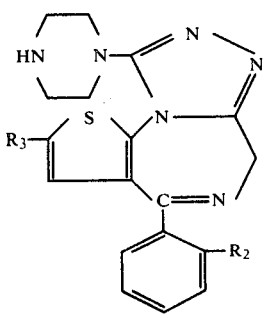
(V)

wherein $R_2$ and $R_3$ have the same meanings as in formula I, with a corresponding carboxylic acid halide or carboxylic acid anhydride.

The acylation reaction is advantageously carried out in the presence of an inert solvent, such as dioxane, tetrahydrofuran, benzene, toluene or xylene; however, an excess of the acylating agent may also serve as the solvent medium. In some cases, it is also of advantage to add an inorganic or organic base, such as potassium carbonate, potassium bicarbonate, pyridine or triethylamine, to the reaction mixture to neutralize the acid released by the reaction.

Depending upon the particular starting material, the reaction time and temperature may vary within wide limits. Thus, the reaction time may be from a few minutes to several hours, and the reaction temperature may range from room temperature to the boiling point of the particular solvent or acylating agent.

In those instances where method A or B yields a compound of the formula I wherein $R_1$ is hydrogen, the same may be converted into the corresponding compound where $R_1$ is alkyl or hydroxyalkyl by alkylation with an alkyl halide, a dialkyl sulfate, an ester of toluene sulfonic acid or an alkyleneoxide. The alkylation is preferably carried out in an inert solvent, such as tetrahydrofuran, dimethylformamide, or a lower alkanol. However, the alkylation may also be performed in the absence of a solvent.

The starting compounds of the formula II for method A are described in the prior art.

The starting compounds of the formula IV for method B may be obtained by reacting a 1-halo-6-phenyl-4H-s-triazolo[3,4-c]thieno[2,3-3]4,1-oxazepine of the formula

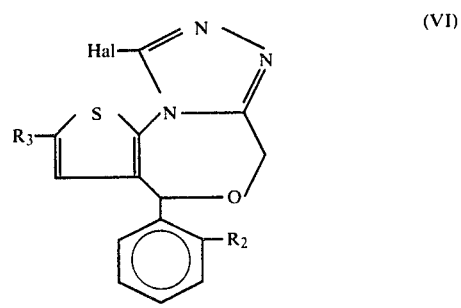
(VI)

wherein
 $R_2$ and $R_3$ have the same meanings as in formula I, and
 Hal is halogen,
with a piperazine of the formula III, followed by exchange of the ring oxygen atom for a nitrogen atom, for instance by the method described in German Offenlegungsschrift No. 2,531,678.

The starting compounds of the formula V for method C may be obtained by reacting a correspondingly substituted 1-halo-6-phenyl-4H-s-triazolo[3,4-c]-thieno[2,3-e]1,4-diazepine with piperazine, or by de-hydrogenating a correspondingly substituted 1-piperazino-7-phenyl-5,6-dihydro-4H-s-triazolo[3,4-c]thieno[2,3-e]1,4-diazepine in analogy to method B.

Those compounds of the formula I where $R_1$ is hydrogen, alkyl, hydroxyalkyl, haloalkyl or dialkylaminoalkyl form stable, water-soluble addition salts with inorganic or organic acids. Examples of non-toxic, pharmacologically acceptable acid addition salts are those formed with a hydrohalic acid, sulfuric acid, phosphoric acid, nitric acid, cyclohexylsulfamic acid, citric acid, tartaric acid, ascorbic acid, maleic acid, formic acid, salicylic acid, methanesulfonic acid, toluenesulfonic acid, 8-chlorotheophylline or the like.

Thus, using the above-described methods, the following compounds of the formula I and, where applicable, their non-toxic acid addition salts may be obtained:
8-bromo-6-(o-chlorophenyl)-1-[N'-(p-chlorophenyl)-piperazino]-4H-s-triazolo[3,4c]thieno[2,3e]1,4-diazepine,
8-bromo-6-(o-chlorophenyl)-1-(N'-phenyl-piperazino)-4H-s-triazolo[3,4c]thieno[2,3e]1,4-diazepine,
8-bromo-6-(o-chlorophenyl)-1-[N'-(o-tolyl)-piperazino]-4H-s-triazolo[3,4c]thieno[2,3e]1,4-diazepine,
8-bromo-6-(o-chlorophenyl)-1-[N'-(o-chlorophenyl)-piperazino]-4H-s-triazolo[3,4c]thieno[2,3e]1,4-diazepine,
8-bromo-6-(o-chlorophenyl)-1-[N'-(2-methoxyphenyl)-piperazino]-4H-s-triazolo[3,4c]thieno[2,3e]1,4-diazepine,
8-bromo-6-(o-chlorophenyl)-1-[N'-(p-fluorophenyl)-piperazino]-4H-s-triazolo[3,4c]thieno[2,3e]1,4-diazepine,
8-bromo-6-(o-chlorophenyl)-1-[N'-(2-hydroxyethyl)-piperazino]-4-H-s-triazolo[3,4c]thieno[2,3e]1,4-diazepine,
8-bromo-6-(o-chlorophenyl)-1-[N'-(o-nitrophenyl)-piperazino]-4H-s-triazolo[3,4c]thieno[2,3e]1,4-diazenine,
8-Bromo-6-(o-bromophenyl)-1-(N'-phenyl-piperazino)-4H-s-triazolo[3,4-c]thieno[2,3e]1,4-diazepine, 8-chloro-6-(o-chlorophenyl)-1-[N'-(3-pyridyl)-piperazino]-4H-s-triazolo[3,4c]thieno[2,3e]1,4-diazepine, 8-bromo-6-(o-chlorophenyl)-1-[N'-(4-pyridyl)-piperazino]-4H-s-triazolo[3,4c]thieno[2,3e]1,4-diazepine, 8-bromo-6-(o-fluorophenyl)-1-piperazino-4H-s-triazolo[3,4c]thieno[2,3e]1,4-diazepine, 8-methyl-6-(o-chlorphenyl)-1-(N'methyl-piperazino)-4H-s-triazolo[3,4-c]thieno[2,3e]1,4-diazepine, 8-bromo-6-(o-chlorophenyl)-1-(N'-ethyl-piperazino)-4H-s-triazolo[3,4c]thieno[2,3-e]1,4-diazepine, 8-bromo-6-(o-chlorophenyl)-1-(N'-isopropyl-piperazino)-4H-s-triazolo[3,4c]thieno[2,3e]1,4-diazepine, 8-bromo-6-(o-bromophenyl)-1-piperazino-4H-s-triazolo[3,4c]-thieno[2,3e]1,4-diazepine, 8-bromo-6-(o-chlorophenyl)-1-[N'-(β-hydroxyisopropyl)-piperazino]4H-s-triazolo[3,4-c]thieno[2,3-e]1,4-diazepine, 8-bromo-6-(o-chlorophenyl)-1-[N'-(β-chloroethyl)-piperazino]-4H-s-triazolo[3,4-c]thieno[2,3-e]1,4-diazepine, 8-chloro-6-(o-chlorophenyl)-1-piperazino-4H-s-triazolo[3,4c]thieno[2,3e]1,4-diazepine, 8-Bromo-6-(o-chlorophenyl)-1-[N'-(2-pyridyl)-piperazino]-4H-s-triazolo[3,4c]-thieno[2,3e]1,4-diazepine, 8-bromo-6-(o-chlorophenyl)-1-[N'-(β-dimethylaminoethyl)-piperazino]-4H-s-triazolo[3,4c]thieno[2,3e]1,4-diazepine, 8-bromo-6-(o-chlorophenyl)-1-[N'-(dimethylaminomethyl)-piperazino]-4H-s-triazolo[3,4c]thieno[2,3e]1,4-diazepine, 8-bromo-6-(o-chlorophenyl)-1-(N'formyl-piperazino)-4H-s-triazolo-[3,4c]thieno[2,3e]1,4-diazepine, 1-(N'-acetyl-piperazino)-8-bromo-6-(o-chlorophenyl)-4H-s-triazolo[3,4c]thieno[2,3e]1,4-diazepine, 1-(N'-acetyl-piperazino)-8-ethyl-6-(o-chlorphenyl)-4H-s-triazolo[3,4c]thieno[2,3e]1,4-diazepine, 1-(N'acetyl-piperazino)-8-chloro-6-(o-chlorphenyl)-4H-s-triazolo[3,4c]thieno[2,3e]1,4-diazepine, 1-(N'-acetyl-piperazino)-8-bromo-6-(o-fluorophenyl)-4H-s-triazolo[3,4c]thieno[2,3-e]1,4-diazepine, 1-(N'-acetyl-piperazino)-8-bromo-6-(o-bromophenyl)-4H-s-triazolo[3,-4c]thieno(2,3-e]-1,4-diazepine, 8-bromo-6-(o-chlorophenyl)-1-[N'-(γ-hydroxypropyl)-piperazino]-4H-s-triazolo[3,4c]thieno[2,3e]1,4-diazepine, 8-bromo-6-(o-chlorophenyl)-1-(N'-stearyl-piperazino)-4H-s-triazolo[3,4c]thieno[2,3e]1,4-diazepine, 8-bromo-1-(N'caproyl-piperazino)-6-(o-chlorphenyl)-4H-s-triazolo[3,4c]thieno[2,3e]1,4-diazepine, 8-bromo-6-(o-chlorophenyl)-1-(N'-benzoyl-piperazino)-4H-s-triazolo[3,4c]thieno[2,3e]1,4-diazepine, 8-bromo-6-(o-chlorophenyl)-1-[N'-(p-fluorobenzoyl)-piperazino]-4H-s-triazolo[3,4c]thieno[2,3e]1,4-diazepine, 8-bromo-6-(o-chlorphenyl)-1-[N'-(o-methylbenzoyl)-piperazino]-4H-s-triazolo[3,4c]thieno[2,3e]1,4-diazepine, 8-bromo-6-(o-chlorphenyl)-1-[N'-(o-chlorobenzoyl)-piperazino]-4H-s-triazolo[3,4c]thieno[2,3e]1,4-diazepine, 8-bromo-6-(o-chlorphenyl)-1-[N'-(p-nitrobenzoyl)-piperazino]-4H-s-triazolo[3,4c]thieno[2,3e]1,4-diazepine, 8-bromo-6-(o-chlorophenyl)-1(N'-nicotinoyl-piperazino)-4H-s-triazolo[3,4c]thieno[2,3e]1,4-diazepine, 8-bromo-6-(o-chlorophenyl)-1-(N'-picolinoyl-piperazino)-4H-s-triazolo[3,4c]thieno[2,3e]1,4-diazepine, and 1-(N'-ethoxycarbonyl-piperazino)-8-bromo-6-(o-chlorphenyl)-4H-s-triazolo[3,4c]thieno[2,3e]1,4-diazepine.

The following examples illustrate the present invention and will enable others skilled in the art to understand it more completely. It should be understood, however, that the invention is not limited solely to the particular examples given below.

EXAMPLE 1

8-Bromo-6-(o-chloro-phenyl)-1-[N'-(β-hydroxy-ethyl)-piperazino]-4H-s-triazolo-[3,4-c]thieno[2,3-3]1,4-diazepine by method A A mixture consisting of 31 gm (0.07 mol) of 1,8-dibromo-6-(o-chloro-phehyl)-4H-s-triazolo[3,4-c]thieno[2,3-e]-1,4-diazepine, 17 gm (0.14 mol) of N-(β-hydroxy-ethyl)-piperazine and 800 ml of xylene was refluxed for 24 hours. Thereafter, while still warm, the reaction mixture was suction-filtered through a mixture of diatomaceous earth and charcoal, and the filtrate was evaporated in vacuo. The residue was taken up in methylene chloride, and the solution was washed with water, dried with sodium sulfate and evaporated, leaving 38.5 gm (81% of theory) of the compound of the formula

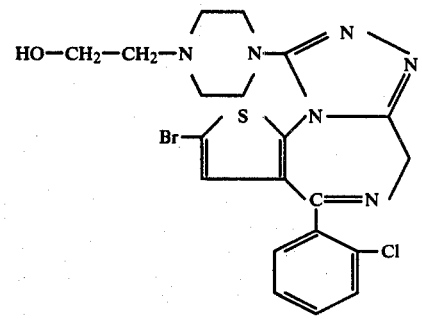

which, after recrystallization from ethyl acetate, had a melting point of 125°–126° C.

The base thus obtained was suspended in a little ethanol, the suspension was admixed with a small excess of ethanolic hydrochloric acid, and ether was added to the mixture, whereupon the readily water-soluble hydrochloride, M.P. 211°–220° C. (decomp.), crystallized out.

In analogous manner, the following acid addition salts were obtained with quantitative yields by dissolving the base in hot ethanol, and adding 1 mol-equivalent of maleic acid, tartaric acid or methanesulfonic acid, respectively, to the solution:

Maleate: M.p. 201°–202° C.;
Tartrate: M.p. 228°–229° C.;
Methanesulfonate: M.p. 241°–242° C.

EXAMPLE 2

8-Bromo-6-(o-chlorophenyl)-1-piperazino-4H-s-triazolo[3,4-c]-thieno[2,3-e]1,4-diazepine by method A 4.5 gm (0.01 mol) of 1,8-dibromo-6-(o-chlorophenyl)-4H-s-triazolo[3,4-c]1,4-diazepine was triturated with 1.8 gm (0.02 mol) of piperazine, and the mixture was heated for 15 minutes at 160° C. After the molten mass had cooled, it was taken up in a mixture of methylene chloride and water, the aqueous phase was separted, and the methylene chloride phase was extracted with a total of 100 ml of 2 N hydrochloric acid. The combined extract solutions were made alkaline with ammonia, the precipitate was again taken up in methylene chloride, and the resulting solution was dried with sodium sulfate and evaporated. The residue was recrystallized from ethyl acetate, yielding 3.8 gm (82% of theory) of the desired base which had a melting point of 246°–248° C.

The hydrochloride, m.p. 240° C. (decomp.) was obtained by acidifying an ethanolic solution of the base with ethanolic hydrochloric acid.

EXAMPLE 3

8-Bromo-6-(o-chlorphenyl)-1-(N'-methyl-piperazino)-4H-s-triazolo[3,4-c]thieno[2,3-c]-1,4-diazepine A mixture consisting of 4.6 gm (0.01 mol) of 8-bromo-6-(o-chlorphenyl)-1-piperazino-4H-s-triazolo[3,4-c]thieno[2,3-e]1,4-diazepine, 1.2 ml (0.02 mol) of methyl iodide and 200 ml of tetrahydrofuran was stirred for three hours at 40°–50° C. Thereafter, the reaction product was isolated from the reaction mixture by column chromatography, yielding 3 gm (63% of theory) of the compound named in the heading, which had a melting point of 206°–208°. Its hydrochlroide, obtained by acidifying an ethanolic solution of the base with ethanolic hydrochloric acid, had a melting point of 210° C. (decomp.).

EXAMPLE 4

8-Bromo-6-(o-chlorophenyl)-1-[N'(2-pyridyl)-piperazino]-4H-s-triazolo[3,4-c]thieno[2,3-e]1,4-diazepine by method A A mixture consisting of 19 gm (0.04 mol) of 1,8-dibromo-6-(o-chlorophenyl)-4H-s-triazolo[3,4-c]thieno[2,3-e]1,4-benzodiazepine, 13.4 gm (0.08 mol) of N-[pyridyl-(2)]-piperazine and 150 ml of xylene was refluxed for 24 hours. Thereafter, the N-[pyridyl-(2)]-piperazine hydrobromide which had precipitated was separated by suction filtration, the filtrate was evaporated, and the residue was recrystallized from ethanol and purified, yielding 13.2 gm (61% of theory) of the compound named in the heading, which had a melting point of 215°–216° C.

EXAMPLE 5

1-(N'-Acetyl-piperazino)-8-bromo-6-(o-chlorophenyl)-4H-s-triazolo[3,4-c]thieno[2,3-e]1,4-diazepine by method C 4.6 gm (0.01 mol) of 8-bromo-6-(o-chlorophenyl)-1-piperazino-4H-s-triazolo[3,4c]thieno[2,3e]1,4-diazepine were stirred in 100 ml of acetic acid anhydride for 20 minutes. The reaction mixture was then poured over ice, and the aqueous mixture was made alkaline with ammonia. The precipitate was taken up in methylene chloride, the methylene chloride phase was dried and evaporated, and the residue was caused to crystallize by addition of ether. Yield: 3.8 gm (76% of theory); m.p. 247°–249° C.

EXAMPLE 6

8-Bromo-6-(o-chlorophenyl)-1-(N'-ethoxycarbonyl-piperazino)-4H-s-triazolo8 3,4c]thieno[2,3e]1,4-diazepine by method C A mixture consisting of 4.6 gm (0.01 mol) of 8-bromo-6-(o-chlorophenyl)-1-piperazino-4H-s-triazolo[3,4c]-thieno[2,3e]1,4-diazepine, 100 ml of tetrahydrofuran, and 2 ml of ethyl chloroformate was stirred for 30 minutes at room temperature. The reaction solution was then evaporated, water and methylene chloride were added to the residue, the mixture was made alkaline with ammonia, and the evaporation residue of the dried methylene chloride phase was chromatographed. Yield: 4.8 gm (91% of theory); M.p. 216°–218° C.

EXAMPLE 7

1-(N'-formyl-piperazino)-8-bromo-6-(o-chlorphenyl)-4H-s-triazolo[3,4c]thieno[2,3e]1,4-diazepine by method C A mixture consisting of 4.6 gm (0.01 mol) of 8-bromo-6-(o-chlorphenyl)-1-piperazino-4H-s-triazolo[3,4-c]thieno[2,3e]1,4-diazepine and 100 ml of formic acid was refluxed for three hours. The solution was poured over ice, the aqueous mixture was made alkaline with 2 N sodium hydroxide, the precipitate was taken up in methylene chloride, and the solution was worked up as described in Example 6. Yield: 3.9 gm (80% of theory); M.p. 205°–215° C.

EXAMPLE 8

8-Bromo-6-(o-chlorophenyl)-1-(N'-methylpiperazino)-4H-s-triazolo[3,4c]thieno[2,3e]1,4-diazepine A mixture consisting of 3.5 gm (0.075 mol) of 1,8-dibromo-6-(o-chlorophenyl)-4H-s-triazolo[3,4c]-thieno[2,3e]4,1-oxazepine, 2 ml of methylpiperazine and 100 ml of xylene was refluxed for 4 hours. Thereafter, the reaction mixture was separated by suction filtration and the filtrate evaporated in vacuo. The residue was taken up in methylene chloride, washed with water, dried, the solvent evaporated and crystallized with isopropylether, yielding 2.9 gm=80% of theory of 8-bromo-6-(o-chlorophenyl)-1-(N'-methylpiperazino)-4H-s-triazolo-[3,4c]thieno[2,3c]4,1-oxazepine of m.p. 150°–153° C.

2.4 gm (0.005 mol) of the oxazepine were stirred 30 minutes with 20 ml of concentrated hydrobromic acid at room temperature. The reaction mixture was then poured on 200 ml of ice-water and the aqueous mixture was made alkaline with ammonia under ice-cooling. Then the precipitate was taken up in methylene chloride, the solution dried and evaporated to a volume of 30 ml. 2.5 ml of thionyl chloride were added and the mixture stirred for 2 hours at room temperature. Then the reaction mixture was evaporated to dryness and the residue was admixed with 30 ml of methanol, which has been saturated with ammonia. After heating for 15 minutes in the autoclave to 60° C., the methanol was evaporated, the residue taken up in methylene chloride and the salts were washed out with water. From the methylene chloride phase the 8-Bromo-6-(o-chlorophenyl)-1-(N'-methylpiperazino)-4H-s-triazolo-[3,4c]thieno[2,3e]5,6-dihydro-1,4-diazepine was obtained and stirred without purification for 4 hours at room temperature with 100 ml of acetone and 1 gm of pulverized potassium permanganate. Then the manganese dioxide was sucked off; the filtrate contained 1.2 gm=50% of theory of the compound named in the heading of m.p. 206°–208° C.

| Example | R₂ | R₃ | R₁ | M.p. °C. |
|---|---|---|---|---|
| 8a | Cl | Br |  phenyl | 248-249 |
| 9 | Cl | Br | 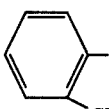 2-CH₃-phenyl | 241-242 |
| 10 | Cl | Br | 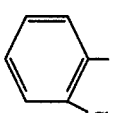 2-Cl-phenyl | 134-135 |
| 11 | Cl | Br | 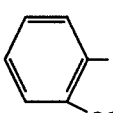 2-OCH₃-phenyl | 218-222 |
| 12 | Cl | Br | 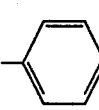 4-F-phenyl | 240-241 |
| 13 | Cl | Br | 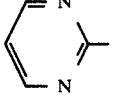 pyrimidinyl | 262-263 |
| 14 | Cl | Br | 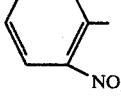 2-NO₂-phenyl | 264 |
| 15 | Br | Br | 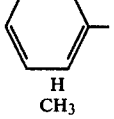 phenyl | 167-169 |
| 16 | F | Br | H | 240-242 |
| 17 | Cl | C₂H₅ | CH₃ | 180-182 |
| 18 | Cl | Br | 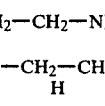 —CH₂—CH₂—N(CH₃)₂ | 224-228 |
| 19 | Cl | Br | Cl—CH₂—CH₂— | 216-217 |
| 20 | Cl | Cl | H | 160-162 (decomp.) |
| 21 | Cl | Br | 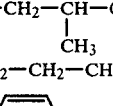 —CH₂—CH(OH)—CH₃ | 222-224 |
| 22 | Cl | Br | —CH₂—CH₂—CH₂—OH | 196-197 |
| 23 | Cl | Br | 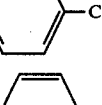 phenyl-CO— | 294 |
| 24 | Cl | Br | 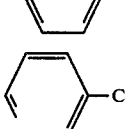 4-F-phenyl-CO— | 311-312 |
| 25 | Cl | Br | 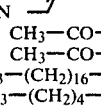 pyridyl-CO— | 247-248 |
| 26 | Cl | C₂H₅ | CH₃—CO— | 220-224 |
| 27 | Cl | Cl | CH₃—CO— | 222-225 |
| 28 | Cl | Br | CH₃—(CH₂)₁₆—CO— | 126-128 |
| 29 | Cl | Cl | CH₃—(CH₂)₄—CO— | 173-175 |
| 30 | Cl | Cl | CH₃—(CH₂)₁₅—CO— | 126-128 |

The compounds of the present invention that is, those embraced by formula I and non-toxic, pharmacologically acceptable acid addition salts of those which form such salts, have useful pharmacodynamic properties. More particularly, they exhibit anxiolytic (anxiety-relieving), tranquilizing, sedative and neuroleptic activities in warm-blooded animals, such as rats and cats. One or another of these activities may predominate in the individual compounds, so that, for example, depending upon the particular type of substitution on the piperazino moiety, the principal activity of some compounds is in the neuroleptic area while that of other compounds is in the sleep-promoting area and so forth.

For instance, those compounds of the formula I wherein $R_1$ is lower alkyl and their water-soluble, non-toxic acid addition salts exhibit primarily anxiolytic properties.

On the other hand, those compounds of the formula I wherein $R_1$ is hydroxy-lower alkyl and their water-soluble, non-toxic acid addition salts exert a favorable influence upon the sleeping-waking pattern of the cat, where the slow-wave-sleep phases are prolonged, the active and relaxing waking phases are shortened, and the REM (rapid eye movement) phases are only slightly increased or remain unchanged.

Those compounds where $R_1$ is acyl or heteroaryl, not only exhibit distinct tranquilizing and anxiolytic properties, but also exert a good effect on the active avoidance reaction in rats, where these two types of activity have chronologically separate maxima. Thus, the neuroleptic property reaches its peak first, and later the anxiolytic property predominates.

Therefore, the novel compounds are especially suitable for the treatment of psychomotoric conditions of excitation and anxiety, as they occur, for example, with schizophrenia, and also for the treatment of convulsions and sleeping disturbances of various origins.

Compounds where $R_1$ is hydrogen, alkyl, hydroxyalkyl, halogenalkyl or dialkylaminoalkyl may, in addition, be converted into stable, water-soluble acid addition salts, whereby a parenteral administration and, therefore, a use of these compounds as short-acting or ultra-short-acting narcotics becomes possible.

Especially effective have proved to be those final products of the formula I, where $R_1$ is hydrogen, alkyl, hydroxalkyl, phenyl, pyridyl or $R_4$—CO—, $R_2$ is chlorine, $R_3$ is bromine and $R_4$ is hydrogen or methyl.

For pharmaceutical purposes the compounds of the present invention are administered to warm-blooded animals peorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.00083 to 0.83 mgm/kg body weight, preferably 0.0016 to 0.42 mgm/kg body weight (oral). The daily dose rate is from 0.083 to 2.5 mgm/kg.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 32

Coated Pills

The pill core composition is compounded from the following ingredients:

| | | |
|---|---|---|
| 8-Bromo-6-(o-chloro-phenyl)-1-[N'-(β-hydroxy-ethyl)-piperazino]-4-H-s-triazolo[3,4-c]thieno[2,3-e]-1,4-diazepine | 1.0 | parts |
| Lactose | 28.5 | parts |
| Corn starch | 19.0 | parts |
| Gelatin | 1.0 | parts |
| Magnesium stearate | 0.5 | parts |
| Total | 50.0 | parts |

Preparation

The triazolo-thieno-diazepine compound, the lactose and the corn starch are intimately admixed with each other, the mixture is granulated through a 1 mm-mesh screen with the aid of an aqueous 10% solution of the gelatin, the granulate is dried and again passed through the screen and the dry granulate is admixed with the magnesium stearate. The resulting composition is compressed into 50 mgm-pill cores which are subsequently coated with a thin shell cnsisting essentially of a mixture of sugar, titanium dioxide, talcum and gum arabic, and finally polished with beeswax. Each coated pill is an oral dosage unit composition containing 1 mgm of the triazolo-thieno-diazepine compound.

EXAMPLE 33

Tablets

The tablet composition is compounded from the following ingredients:

| | | |
|---|---|---|
| 8-Bromo-6-(o-chloro-phenyl)-1-[N'-(2-pyridyl)-piperazino]-4H-s-triazolo-[3,4-c]thieno[2,3-3]-1,4-diazepine | 0.5 | parts |
| Lactose | 50.0 | parts |
| Corn starch | 43.5 | parts |
| Soluble starch | 5.0 | parts |
| Magnesium stearate | 1.0 | parts |
| Total | 100.0 | parts |

Preparation

The active ingredient and magnesium stearate are granulated with an aqueous solution of the soluble starch, the granulate is dried and admixed thoroughly with lactose and corn starch. Then the mixture is pressed to tablets of 100 mg of weight, each tablet comprising 0.5 mg of active ingredient.

EXAMPLE 34

Suppositories 1 suppository comprises

| | |
|---|---|
| Active ingredient according to the invention | 5,0 mg |
| suppository mass | 1.695,0 mg |

Preparation

The suppository base is melted and cooled to 40° C., the finely pulverized triazolo-thieno-diazepine compound is stirred into the suppository base with the aid of an immersion homogenizer, and 1700 mgm-portions of the resulting mixture at 35° C. are poured into cooled suppository molds and allowed to harden therein. Each suppository is a rectal dosage unit composition containing 5 mgm of the thiazolo-thieno-diazepine compound.

EXAMPLE 35

Hypodermic Solution

The solution is compounded from the following ingredients:

| | | |
|---|---|---|
| 8-Bromo-6-(o-chloro-phenyl)-1-[N'-(2-hydroxy-isopropyl)-piperazino]-4H-s-triazolo[3,4-c]thieno[2,3-e]-1,4-diazepine | 0.5 | parts |
| Sodium pyrosulfite | 1.0 | parts |
| Disodium salt of EDTA | 0.5 | parts |
| Sodium chloride | 8.5 | parts |
| Double-distilled water q. s. ad | 1000.0 | parts |

Preparation

The active ingredient and the excipients are dissolved in a sufficient amount of double-distilled water, and the remaining amount of water is added, the solution is filtered, and the filtrate is filled into 1 cc ampules under aseptic conditions, which are then sterilized and sealed. The contents of each ampule are an injectable dosage unit composition containing 0.5 mgm of the active ingredient.

Any one of the other compounds embraced by formula I or, where applicable, a non-toxic, pharmacologically acceptable acid addition salt thereof may be substituted for the particular active ingredient in Examples 32 through 35. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others—skilled in the art that the invention is not limited to these particular embodiments, and that various changes and modifications may be made without departing from the spirit of the invention or the scope of the appended claims.

We claim:

1. A compound of the formula

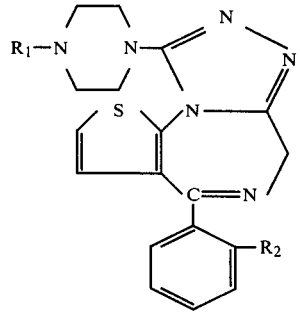

wherein
R₁ is hydrogen, lower alkyl, halo-lower alkyl, hydroxy-lower alkyl, di(lower alkyl)amino-lower alkyl, phenyl, tolyl, methoxy-phenyl, nitro-phenyl, halo-phenyl, pyridyl, pyrimidinyl or —CO—R₄, where R₄ is hydrogen, alkyl or 1 to 17 carbon atoms, alkoxy of 1 to 2 carbon atoms, phenyl, tolyl, methoxy-phenyl, halo-phenyl, nitro-phenyl or pyridyl;

$R_2$ is hydrogen, fluorine, chlorine, or bromine; and $R_3$ is chlorine, bromine or lower alkyl;

or, when $R_1$ is hydrogen, lower alkyl, hydroxy-lower alkyl, halo-lower alkyl or di(lower alkyl)amino-lower alkyl, a non-toxic, pharmacologically acceptable acid addition salt thereof.

2. A compound of claim 1, where $R_1$ is hydrogen, alkyl of 1 to 3 carbon atoms or hydroxy-alkyl of 1 to 3 carbon atoms;

$R_2$ is chlorine; and $R_3$ is bromine;

or a non-toxic, pharmacologically acceptable acid addition salt thereof.

3. A compound of claim 1, where $R_1$ is phenyl or pyridyl, $R_2$ is chlorine, and $R_3$ is bromine.

4. A compound of claim 1, where $R_1$ is formyl or acetyl $R_2$ is chlorine, and $R_3$ is bromine.

5. A compound of claim 2, which is 8-bromo-6-(o-chloro-phenyl)-1-[(N'-(β-hydroxy-ethyl)-piperazino]-4H-s-triazolo[3,4-c]thieno[2,3-e]1,4-diazepine or a non-toxic, pharmacologically acceptable acid addition salt thereof.

6. The compound of claim 3, which is 8-bromo-6-(o-chloro-phenyl)-1-[N'-(2-pyridyl)-piperazino]-4H-s-triazolo[3,4-c]thieno[2,3-e]1,4-diazepine.

7. A compound of claim 2, which is 8-bromo-6-(o-chloro-phenyl)-1-[N'-(2-hydroxy-propyl)-piperazino]-4H-s-triazolo[3,4-c]thieno[2,3-e]1,4-diazepine or a non-toxic, pharmacologically acceptable acid addition salt thereof.

8. A compound of claim 2, which is 8-bromo-6-(o-chloro-phenyl)-1-[N'-(2-hydroxy-isopropyl)-piperazino]-4H-s-triazolo[3,4-c]thieno[2,3-c]1,4-diazepine or a non-toxic pharmacologically acceptable acid addition salt thereof.

9. An anxiolytic, tranquilizing, sedative or neuroleptic pharmaceutical dosage unit composition consisting essentially of an inert pharmaceutical carrier and an effective anxiolytic, tranquilizing, sedative or neuroleptic amount of a compound of claim 1.

10. The method relieving anxiety and tension, allaying excitement or inducing sleep in a warm blooded animal in need thereof, which comprises perorally, parenterally or rectally administering to said animal an effective anxiolytic, tranquilizing, sedative or neuroleptic amount of a compound of claim 1.

* * * * *

UNITED STATES PATENT AND TRADEMARK OFFICE
CERTIFICATE OF CORRECTION

PATENT NO. : 4,180,573
DATED : December 25, 1979
INVENTOR(S) : KARL-HEINZ WEBER ET AL.

It is certified that error appears in the above-identified patent and that said Letters Patent are hereby corrected as shown below:

Column 12, Claim 1:   The portion of the structural formula which reads

" 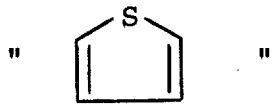 "

should read

-- 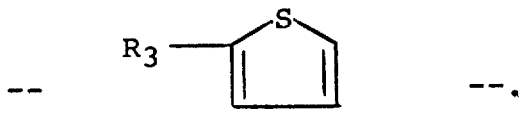 --.

Signed and Sealed this

First Day of April 1980

[SEAL]

Attest:

SIDNEY A. DIAMOND

*Attesting Officer*   *Commissioner of Patents and Trademarks*